(12) United States Patent
Demers

(10) Patent No.: US 7,131,947 B2
(45) Date of Patent: Nov. 7, 2006

(54) VOLUMETRIC ULTRASONIC IMAGE SEGMENT ACQUISITION WITH ECG DISPLAY

(75) Inventor: Douglas Armand Demers, Haverhill, MA (US)

(73) Assignee: Koninklijke Philips Electronics N.V., Eindhoven (NL)

(*) Notice: Subject to any disclaimer, the term of this patent is extended or adjusted under 35 U.S.C. 154(b) by 211 days.

(21) Appl. No.: 10/816,332

(22) Filed: Apr. 1, 2004

(65) Prior Publication Data

US 2004/0225219 A1 Nov. 11, 2004

Related U.S. Application Data

(60) Provisional application No. 60/468,719, filed on May 8, 2003.

(51) Int. Cl.
*A61B 8/00* (2006.01)
(52) U.S. Cl. .................... 600/447; 128/916
(58) Field of Classification Search ........ 600/440–441, 600/443, 447; 128/916
See application file for complete search history.

(56) References Cited

U.S. PATENT DOCUMENTS

| | | | | |
|---|---|---|---|---|
| 3,909,792 A * | 9/1975 | Harris et al. | ............... | 600/519 |
| 3,951,135 A * | 4/1976 | Goldberg et al. | ............ | 600/523 |
| 5,159,931 A * | 11/1992 | Pini | .......................... | 600/443 |
| 5,551,434 A * | 9/1996 | Iinuma | ........................ | 600/455 |
| 5,813,986 A * | 9/1998 | Ubukata | ...................... | 600/440 |
| 5,993,390 A | 11/1999 | Savord et al. | | |
| 5,997,479 A | 12/1999 | Savord et al. | | |
| 6,139,500 A * | 10/2000 | Clark | ........................ | 600/443 |
| 6,375,617 B1 | 4/2002 | Fraser | | |
| 6,409,659 B1 * | 6/2002 | Warner et al. | .............. | 600/300 |
| 6,447,450 B1 * | 9/2002 | Olstad | ........................ | 600/437 |
| 6,447,453 B1 * | 9/2002 | Roundhill et al. | .......... | 600/443 |
| 6,544,175 B1 * | 4/2003 | Newman | ..................... | 600/437 |
| 6,558,325 B1 * | 5/2003 | Pang et al. | .................. | 600/443 |
| 6,665,559 B1 * | 12/2003 | Rowlandson | ............... | 600/515 |
| 6,673,017 B1 * | 1/2004 | Jackson | ...................... | 600/437 |
| 6,709,394 B1 | 3/2004 | Frisa et al. | | |
| 6,730,032 B1 * | 5/2004 | Yamauchi | ................... | 600/443 |
| 6,966,878 B1 * | 11/2005 | Schoisswohl et al. | ....... | 600/443 |
| 2005/0090745 A1 * | 4/2005 | Steen | ........................ | 600/447 |

* cited by examiner

*Primary Examiner*—Francis J. Jaworski
(74) *Attorney, Agent, or Firm*—Tony Piotrowski

(57) ABSTRACT

A three dimensional ultrasonic imaging system acquires volume segments of a wide field of view volume image in coincidence with an ECG waveform. The ECG waveforms acquired during acquisition of the volume segments are displayed in a comparative display in which a different ECG waveform can be visually distinguished. A volume segment acquired during an arrhythmic heartbeat can be reacquired or replaced in the wide field of view volume data set. The ECG waveforms can be displayed vertically aligned by their R-waves, in overlapping alignment, or differently shaded or colored. A processor can compare the ECG waveforms automatically and automatically replace the data of a volume segment acquired during an arrhythmic heartbeat.

16 Claims, 10 Drawing Sheets

VOLUMETRIC ULTRASONIC IMAGE SEGMENT ACQUISITION WITH ECG DISPLAY

This invention claims the benefit of Provisional U.S. patent Application Ser. No. 60/468,719, filed May 8, 2003.

This invention relates to medical ultrasound imaging and, more particularly, to three dimensional volumetric image acquisition with ECG gating and display.

U.S. Pat. No. 5,993,390, the contents of which are incorporated herein by reference, describes a method and apparatus for acquiring a three dimensional (3D or volumetric) ultrasonic image with a wide field of view and high temporal resolution. In the method of this patent, ultrasound image data representative of three-dimensional volume segments of an image volume of interest is acquired in synchronism with corresponding cardiac cycles of a patient. The image data representative of the volume segments is combined to provide image data representative of a three-dimensional image of a wide field image volume. The image data acquisition may be synchronized to a selected phase of the patient's cardiac cycle, so that the image data sets represent the image volume at the selected phase. Image data for a three-dimensional volume segment may be acquired during each of the cardiac phases of a cardiac cycle so that the resulting wide field of view image can be replayed as a real-time volumetric image of anatomy such as the beating heart.

The volume segment data of this patent may be acquired by sweeping a one dimensional array transducer over a volumetric region of the body or by electronically steering beams from a two dimensional array transducer over the volumetric region. Electronic steering provides an advantage in that the volume segments and hence the entire wide field volumetric region can be scanned in a short amount of time, enabling the production of high quality temporally resolved images.

The highest quality wide field of view images will be acquired when the subject is exhibiting a uniform heartbeat. This is because acquisition of the different cardiac phases of each volume segment is triggered or gated from an ECG cardiac signal. If the subject's heart cycle is arrhythmic the volume segments will not exhibit matching phased data sets, leading to artifacts in the wide field of view image. Accordingly it would be desirable to know when ultrasonic acquisition is being affected by arrhythmic conditions so that resulting artifacts in the volumetric image can be prevented or eliminated.

In accordance with the principles of the present invention, volumetric cardiac imaging is performed by ECG gating of the acquisition of volume segments. The ECG waveforms of the acquisition of different volume segments are displayed to provide an indication of the uniformity of the segment acquisition. The ECG waveforms may be displayed comparatively in various ways to better enable the detection of an arrhythmic heart cycle. The corresponding volume segment may then be replaced or reacquired. In accordance with a further aspect of the present invention, the ECG waveforms are automatically analyzed to detect an arrhythmic acquisition, and a flawed volume segment is automatically replaced or reacquired in the volumetric image.

Figure 1:
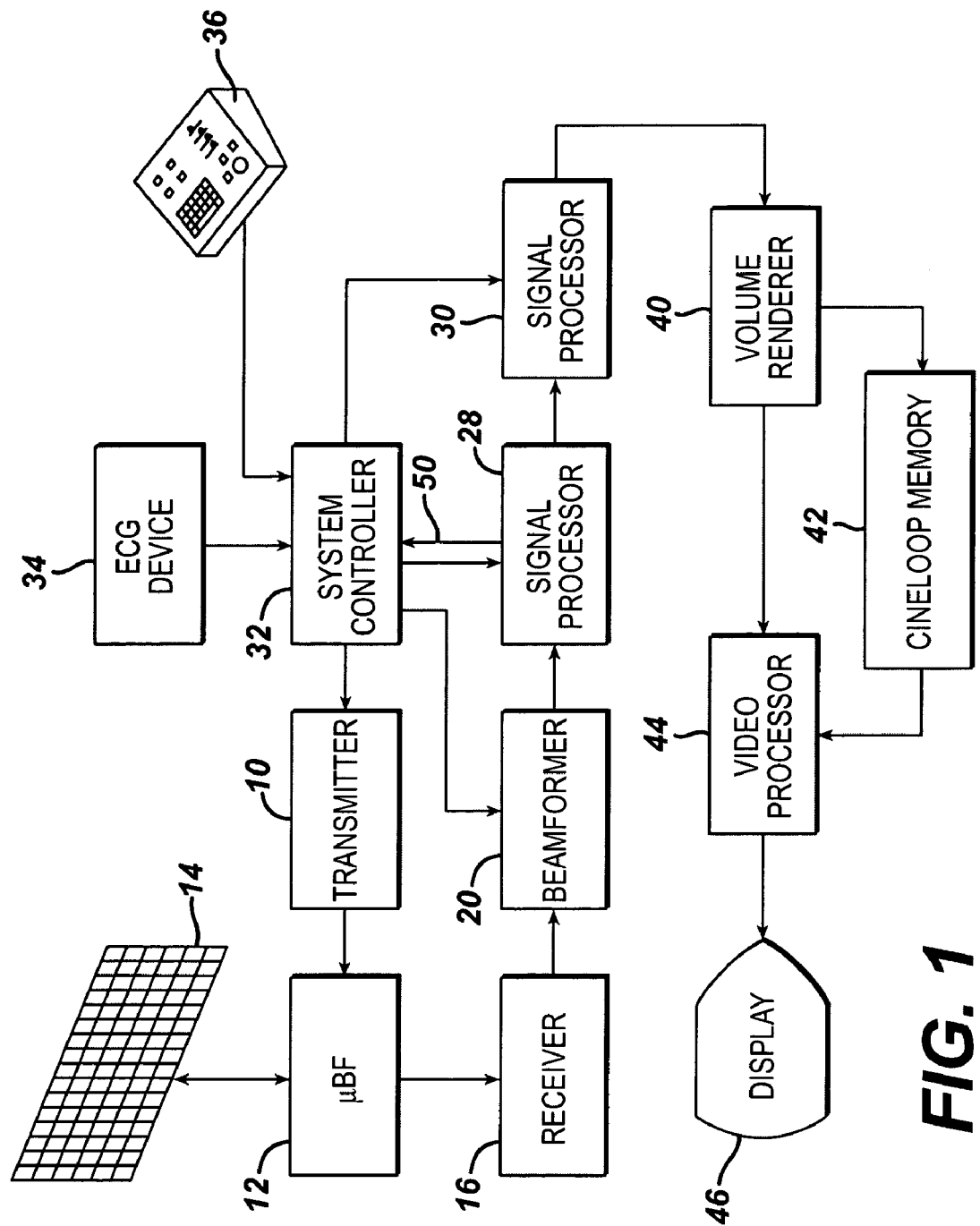
FIG. 1 is a block diagram of an example of an ultrasound imaging system suitable for implementing the present invention.

A block diagram of an ultrasound imaging system constructed in accordance with the principles of the present invention is shown in FIG. 1. An ultrasound transmitter 10 is coupled to a microbeamformer 12 for a transducer array 14. Microbeamformers, also called subarray beamformers, are described more fully in U.S. Pat. Nos. 5,997,479 and 6,375,617. Transducer array 14 may be a two-dimensional array of transducer elements for performing three-dimensional scanning. The transducer array 14 responds to transmit signals from the transmitter and the microbeamformer by transmitting ultrasound energy into a region being imaged and receives reflected ultrasound energy, or echoes, from various structures and organs within the patient's body. The transmitter 10 and/or the microbeamformer 12 includes a transmit beamformer. By appropriately delaying the pulses applied to each transducer element, the transmitter 10 and/or the microbeamformer 14 causes the array transducer 14 to transmit a focused ultrasound beam along a desired transmit scan line.

The transducer array 14 is coupled to an ultrasound receiver 16. Reflected ultrasound energy from a given point within the patient's body is received by the transducer elements at different times. The transducer elements convert the received ultrasound energy to received electrical signals which are amplified by receiver 16 and are supplied to a receive beamformer 20. The signals from each transducer element are individually delayed and then are summed in groups by the microbeamformer 12, the signals from which are delayed and summed by the beamformer 20 to provide a beamformer signal that is a representation of the reflected ultrasound energy level along a given receive scan line. As known in the art and discussed in the aforementioned U.S. Pat. No. 6,375,617, the delays applied to the received signals may be varied during reception of ultrasound energy to effect dynamic focusing. The process is repeated for multiple scan lines to provide signals for generating the data set for an image of a region of interest in the patient's body. Because the transducer array is two-dimensional, the receive scan lines can be steered in azimuth and in elevation to form a three-dimensional scan pattern.

The beamformer signals are processed by a signal processor 28 which may perform functions such as filtering, harmonic signal separation, speckle reduction, or Doppler processing. The processed signals from the scan lines are stored in a 3D image data buffer 30 which, as described below, stores image data for different volume segments of an image volume and for different cardiac phases of a cardiac cycle. The image data is output. from image data buffer 30 to a volume renderer 40 which produces a volume rendering of the scanned volumetric region from a desired viewing perspective. Volume renderings of the full volumetric region are produced for each acquired phase of the cardiac cycle and stored in a Cineloop memory 42. The images stored in the Cineloop memory are generally referred to as a loop, because the usual mode of display is to replay the images in a repeating cycle or loop. The images stored in the Cineloop memory, or an image produced by the volume renderer 40, are applied to a video processor 44. The video processor 44 produces the appropriate drive signals for display of the volumetric images on a display 46. The ultrasound system may also include a scan converter which converts linear or sector scan signals from beamformer 20 to conventional raster scan display signals. The scan converter may be used to produce images in the three dimensional imaging mode known as the "biplane mode," as more fully described in U.S. Pat. No. 6,709,394.

A system controller 32 provides overall control of the system. The system controller 32 performs timing and control functions and typically includes a microprocessor and associated memory. The system controller responds to user inputs from a control panel 36 or display screen soft keys or menus to cause the circuitry of the ultrasound system to perform the functions commanded by the user.

An ECG device 34 includes ECG electrodes attached to the patient. The ECG device 34 supplies ECG waveforms to system controller 32 for synchronizing imaging to the patient's cardiac cycle, as described in detail below. In accordance with the principles of the present invention the ECG waveforms of different volume segments are displayed or processed to produce improved multi-segment volumetric images, examples of which are described below.

Figure 3:
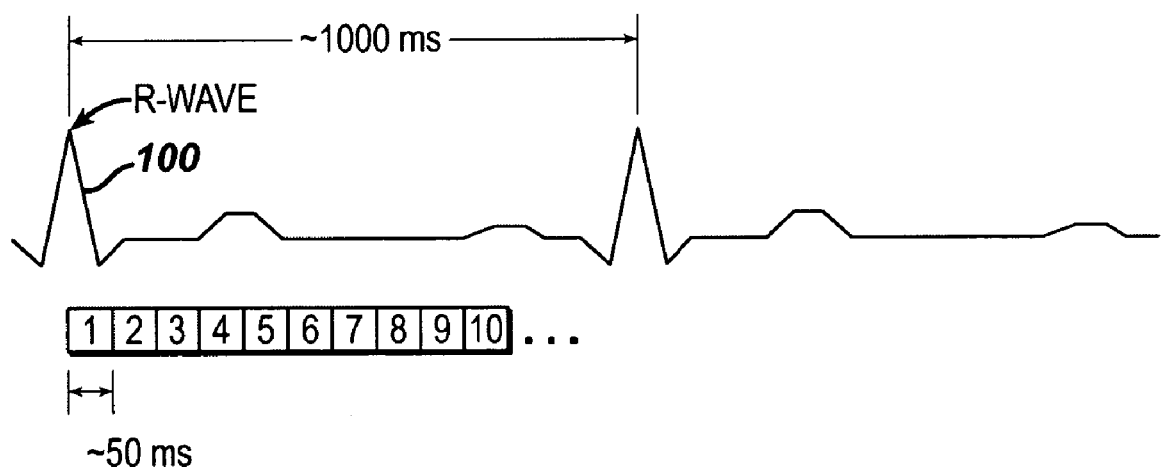
FIG. 3 shows an ECG waveform that is divided into a plurality of cardiac phases.

The present invention is based on the acquisition of image data for one or more volume segments in synchronism with the patient's cardiac cycle. An example of an ECG waveform is shown in FIG. 3. In the example of FIG. 3, ECG waveform 100 indicates a heartbeat every second or every 1000 milliseconds. The cardiac cycle may be divided into cardiac phases for imaging. For example, 20 cardiac phases of approximately 50 milliseconds each may be utilized. The selection of the cardiac phase duration is typically based on the maximum time in which the heart does not move significantly. More or fewer cardiac phases may be utilized. At the time of each cardiac phase, based upon the R-wave time, a volume segment is scanned to image the segment as it appears at that phase of the heart cycle. The greater the number of phases, the smoother and more temporally resolved is the appearance of the real time cardiac image.

By obtaining a three-dimensional image representing the heart in each of the cardiac phases, a variety of information can be obtained. The three-dimensional images of the heart at successive cardiac phases can be displayed as a function of time to represent heart movement. The moving image can be used to identify end systole and end diastole and to perform other diagnostics. Images for a selected cardiac phase can be rotated to a desired orientation for improved analysis. Image analysis techniques can be utilized to quantify maximum and minimum volumes of the left ventricle. From this information, ejection volume and ejection fraction can be calculated.

In accordance with an aspect of the present invention, image data for different three-dimensional volume segments of the image volume is acquired during successive cardiac cycles until a complete image is acquired. The ECG waveform 100 of the patient is used to trigger image data acquisition, so that data acquisition is synchronized to the patient's cardiac cycle. More specifically, image data acquisition is synchronized to a specific phase of the cardiac cycle. Furthermore, image data may be acquired during each phase of each cardiac cycle. The amount of image data acquired during each cardiac phase is a function of the duration of the cardiac phase and the speed of image data acquisition.

Figure 2:
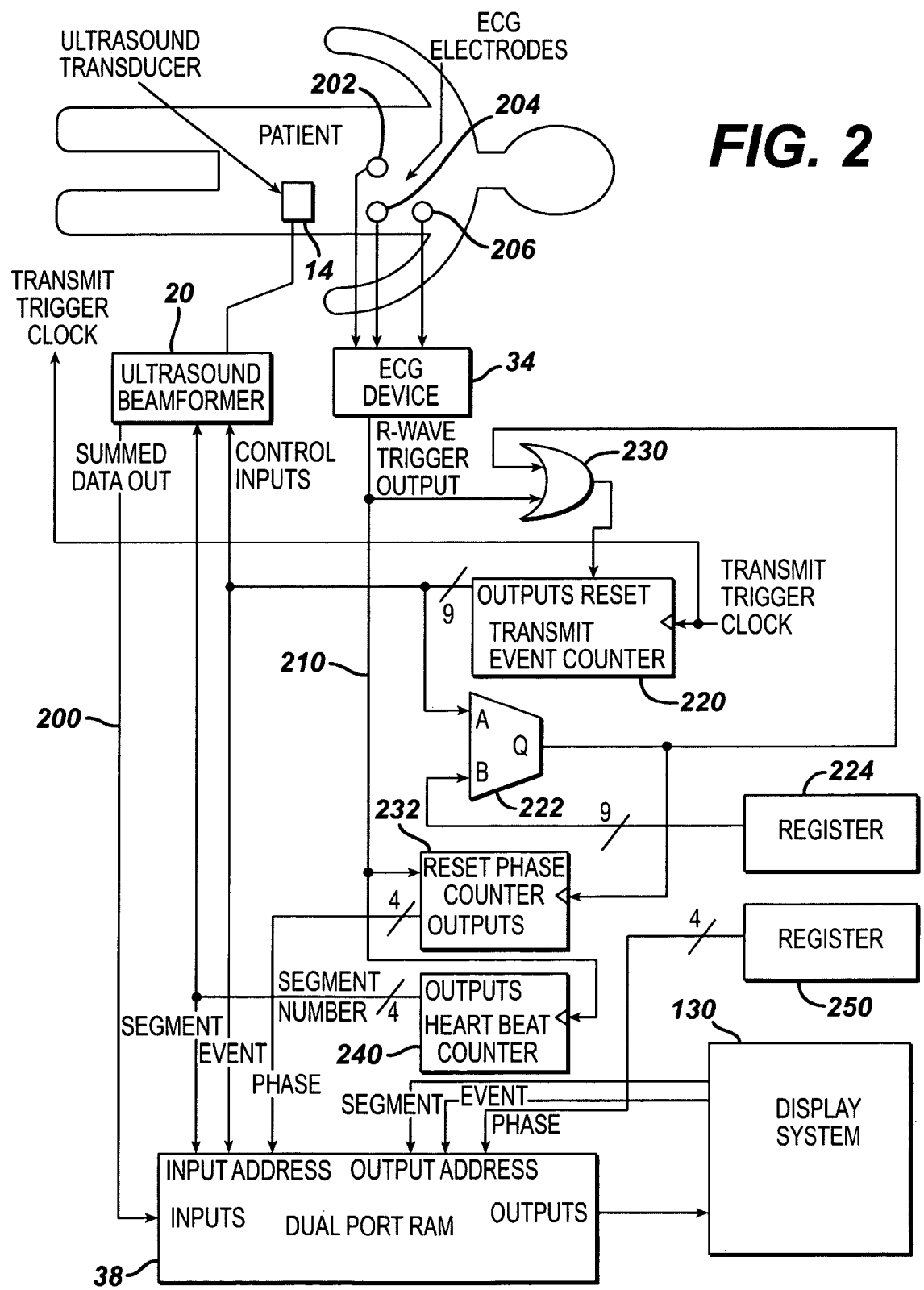
FIG. 2 is a schematic block diagram of an example of a system for cardiac ultrasound imaging in accordance with the invention.
Figure 7:
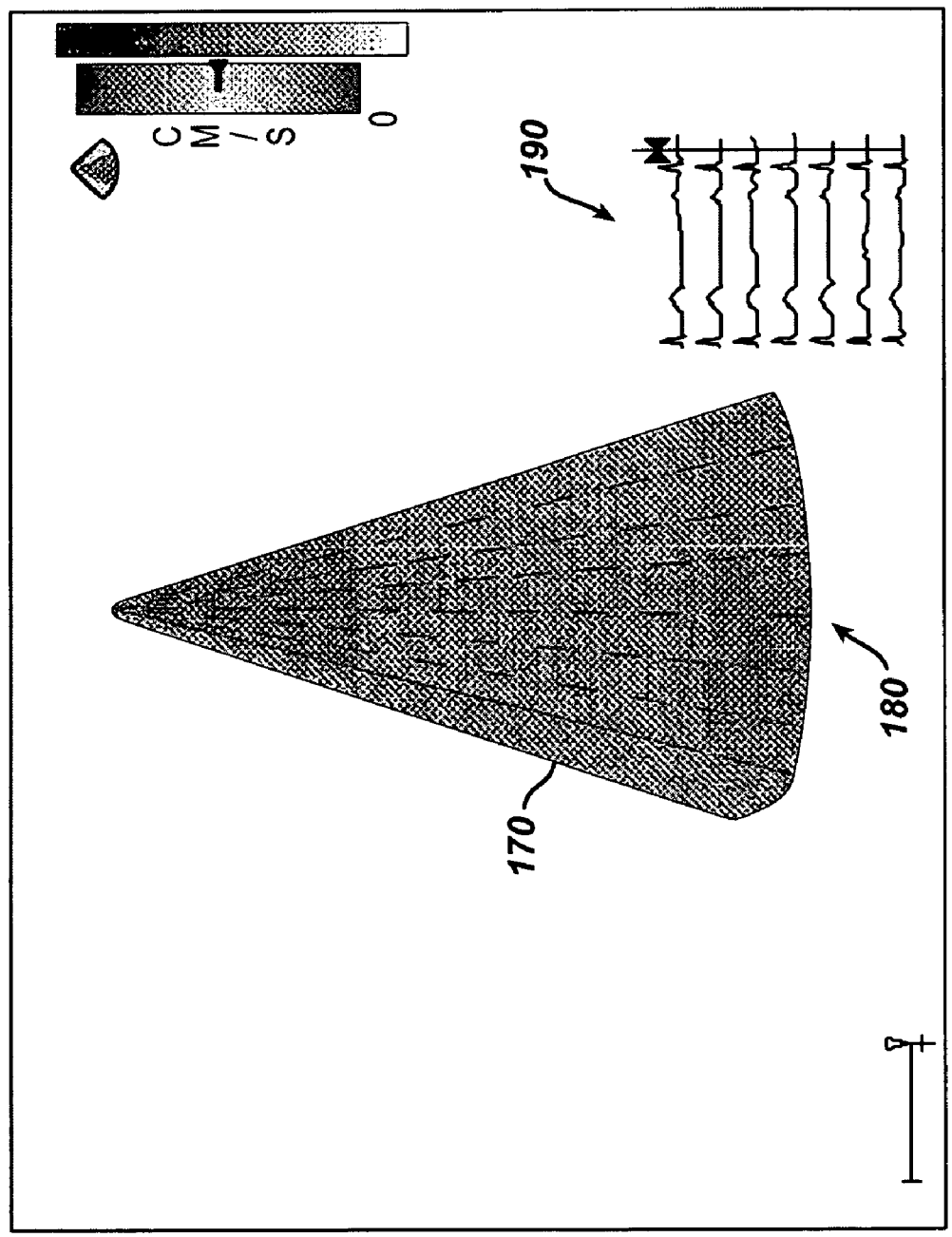
FIG. 7 shows a second embodiment of an ultrasound display of a wide field of view volumetric image that is composed of volume segments and accompanied by a differentiated ECG display.

A simplified block diagram of a system for implementing segmented, three-dimensional cardiac imaging in accordance with the present invention is shown in FIG. 2. Like elements in FIGS. 1 and 2 have the same reference numerals. Ultrasound energy is transmitted into the region of interest in the patient by transducer array 14. Transmitter 10, microbeamformer 12 and receiver 16 are not shown in FIG. 7 for ease of understanding. The received ultrasound echoes are processed by beamformer 20 to provide image data on line 200. The image data is stored in image data buffer 38, which in the example of FIG. 7 is a dual port random access memory (RAM).

ECG electrodes 202, 204 and 206, attached to the patient, sense the patient's cardiac cycle and provide signals to ECG device 34. The ECG device 34 provide an R-wave trigger output on line 210. The R-wave trigger output corresponds to the peak of the ECG waveform 100 shown in FIG. 3.

A transmit trigger clock, which provides one pulse for each transmit event, is supplied to a transmit event counter 220 and to transmitter 10 (FIG. 1). The outputs of transmit event counter 220 are supplied to beamformer 20, to an event input address of image data buffer 38 and to a first input of a comparator 222. A register 224 stores the number of transmit events per cardiac phase. The outputs of register 224 are supplied to a second input of comparator 222. The output of comparator 222 is asserted when transmit event counter 220 reaches a count equal to the value stored in register 224. Thus, the output of comparator 222 is asserted when the desired number of transmit events has been reached in each cardiac phase. The output of comparator 222 is supplied to a first input of OR gate 230 and to the clock input of a cardiac phase counter 232. The outputs of phase counter 232, which indicate the cardiac phase for which image data is being acquired, are supplied to a phase input address of image data buffer 38.

The R-wave trigger output of ECG device 34 is supplied to a second input of OR gate 230, to the reset input of phase counter 232 and to the clock input of a heartbeat counter 240. The heartbeat counter 240 is incremented by the patient's heartbeats. The outputs of heartbeat counter 240 are supplied to a segment input address of image data buffer 38 and indicate the volume segment for which image data is being acquired. Thus, the input address of image data buffer 28 is made up of a segment input address which indicates volume segment, a phase input address which indicates cardiac phase and an event input address which indicates the transmit event within a specific volume segment and cardiac phase. The dual port RAM of image data buffer 38 may have locations for storage of image data corresponding to each transmit event of each volume segment of the image volume and corresponding to each phase of the patient's cardiac cycle.

The OR gate 230 supplies an output to the reset input of transmit event counter 220. Thus, transmit event counter is reset by the patient's heartbeat or when the comparator 222 indicates that the required number of transmit events has been completed for the current cardiac phase.

The output from image data buffer 38 is controlled by display system 130. Image data buffer 38 receives an output address, including a segment output address and an event output address from display system 130, and a cardiac phase output address from a register 250. Register 250 contains a value that indicates the cardiac phase to be displayed. The display system 130 combines the image data for the volume segments of the selected cardiac phase to produce a three-dimensional image of the image volume. By incrementing the value in register 250, three-dimensional images of different cardiac phases may be displayed in sequence. By incrementing to successive images at a suitable rate, real time images of heart movement may be displayed.

The control components of the imaging system of FIG. 2, including transmit event counter 220, comparator 222, OR gate 230, phase counter 232, heartbeat counter 240 and registers 224 and 250, may constitute part of system controller 32 (FIG. 1). It will be understood that the functions performed by these control components may be performed by a programmed microcomputer within the scope of the invention.

Figure 5:
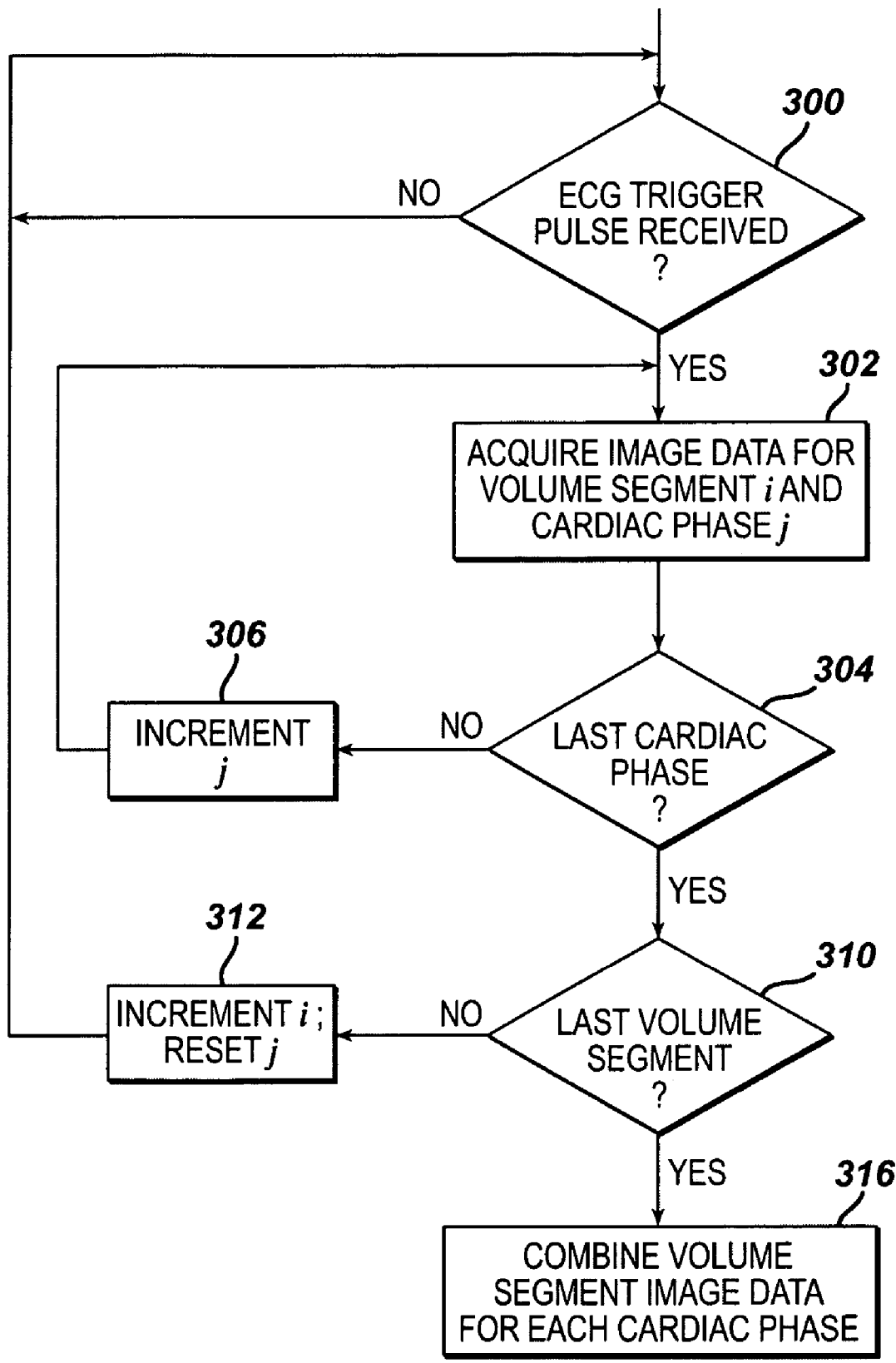
FIG. 5 is a flow diagram of an example of a method for cardiac ultrasound imaging in accordance with the present invention.

A flowchart of a process for segmented three-dimensional cardiac imaging in accordance with the present invention is shown in FIG. 5. When an ECG trigger pulse is received, as determined in step 300, image data is acquired for volume segment i and cardiac phase j in step 302. The data acquisition step 302 involves generation of the specified number of transmit events for the volume segment, processing the received signals in beamformer 20 to provide image data and storing the image data in image data buffer 38. In step 304, a determination is made as to whether the current cardiac phase is the last cardiac phase in the cardiac cycle. When the current cardiac phase is not the last cardiac phase, a cardiac phase index j is incremented in step 306, and the process returns to step 302 for acquisition of image data for the next cardiac phase of the same cardiac cycle. When the current cardiac phase is the last cardiac phase, a determination is made in step 310 as to whether image data has been acquired for the last volume segment of the image volume. When the current volume segment is not the last volume segment, a volume segment index i is incremented and the cardiac phase index j is reset in step 312. The process then returns to step 300 to wait for the next ECG trigger pulse.

The process of FIG. 5 performs image data acquisition for one or more volume segments during each phase of the patient's cardiac cycle. Complete three-dimensional images of each cardiac phase are acquired in a relatively small number of heartbeats. When image data for all volume segments of the image volume has been acquired, the volume segment image data is combined in step 316 to provide a composite data set for each of the cardiac phases. The combining step involves combining image data for the volume segments of the image volume in the respective cardiac phases. The composite data sets are volume rendered and the resulting wide field of view volumetric images are displayed.

One way to scan the segments is to scan each segment up to its boundary with an adjoining segment, then combine the segments by abutting adjacent sides of the data set. This approach relies upon the spatial steering accuracy of the beams to produce smoothly abutting volume segments. However, this accuracy will not pertain if the scanhead is moved during acquisition or there is motion such as that from patient breathing. In such circumstances the volume segments may not smoothly align adjacent to each other. This problem may be overcome by overscanning each volume segment such that adjoining segments overlap. This approach requires somewhat more time for image data acquisition. However, the volume segments may be aligned by analyzing sets of image data in overlapping portions of the volume segments to determine offset error and shifting the image data in different volume segments so as to reduce the offset error. An example of such analysis is the MSAD analysis described in U.S. Pat. No. 6,442,289.

Figure 4:
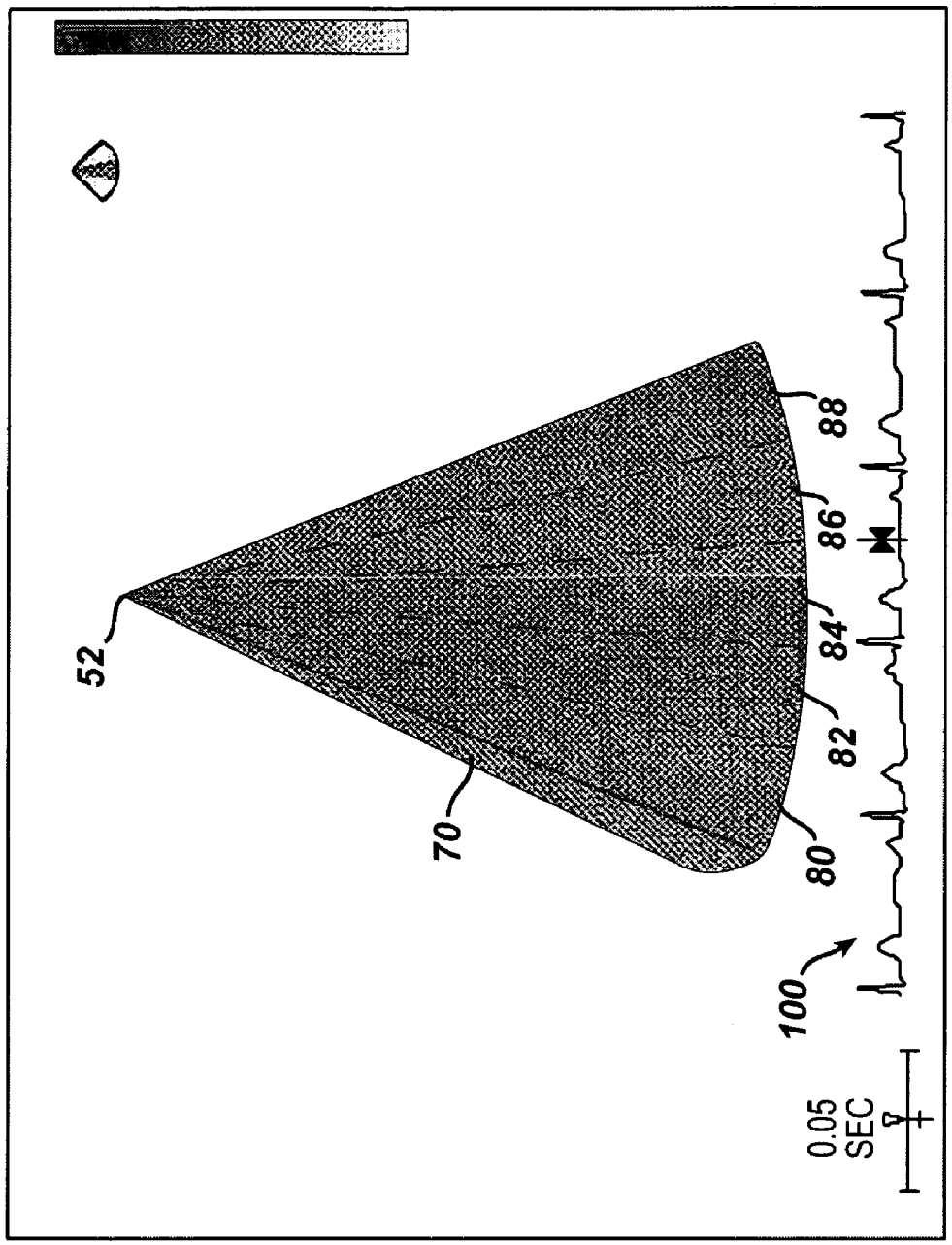
FIG. 4 shows an ultrasound display of a wide field of view volumetric image as acquired by the ultrasound system of FIGS. 1 and 2.

An example of a three-dimensional image volume 70 for which an image may be acquired in accordance with the present invention is shown in the ultrasound display of FIG. 4. An image volume 70 may have a conical or pyramidal shape with an apex 52 centered on transducer array 14 (above; not shown). dimensional ultrasound imaging during which a volume segment 80, 82, 84, 86 and 88 is acquired during each heart cycle of an ECG waveform 100. Volume 70 may, for example, be imaged as a plurality of two-dimensional sector-shaped slices. The diameter of image volume 70 may be defined in terms of the required number of receive lines to achieve a desired resolution. The required number of receive lines to acquire a complete image of volume 70 is given by $(nL^2)/4$, where L is the diameter of a conical image volume 70 in units of receive lines. Thus, for example, where image volume 70 has a diameter of 120 receive lines, 11,304 receive lines are needed to acquire image data for a conical volume 70. The present invention is particularly suitable for cardiac imaging. To facilitate cardiac imaging, image volume 70 may be divided into three-dimensional volume segments 80–88 for volumetric imaging of the patient's heart.

The image data stored in image data buffer 38 is organized and combined and rendered to form a three-dimensional image of the image volume 70 in each cardiac phase. Thus, image data for volume segments 80 through 88, acquired during the corresponding cardiac phase of five cardiac cycles is combined to provide a three-dimensional image 70 of that cardiac phase. Similarly, image data for volume segments 80 through 88 acquired during a second cardiac phase of the five cardiac cycles is combined to provide a three-dimensional image 70 of the second cardiac phase. The same approach is used for the other cardiac phases during which image data is acquired. Thus, for example twenty three-dimensional images 70 of the twenty cardiac phases are obtained in five heartbeats in this example. It will be appreciated that other time interleaved acquisition sequences of the volumetric region may alternatively be employed or may be distributed over a greater number of heart cycles.

The image volume 70 may be divided into a different number of volume segments. Furthermore, the cardiac cycle may be divided into a different number of cardiac phases. Image data for a single larger volume segment or for two or more smaller volume segments may be acquired during a cardiac cycle. The selection of these parameters depends on a number of factors, including the desired resolution, the imaging speed, i.e., the time to acquire a complete three-dimensional image, and the size of the image volume. Further details of segmented three-dimensional cardiac imaging may be found in the U.S. Pat. No. 5,993,390.

Figure 6:
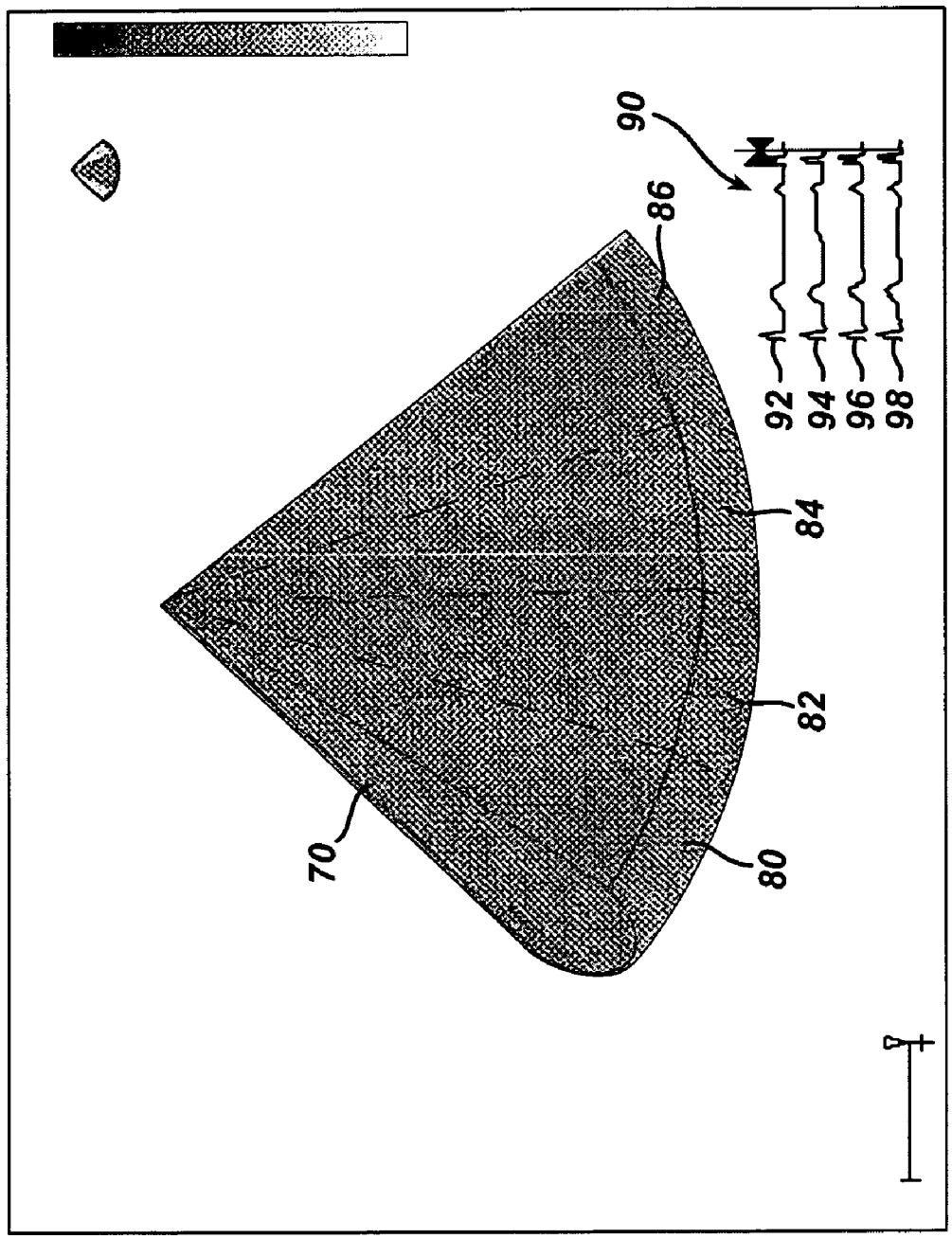
FIG. 6 shows a first embodiment of an ultrasound display of a wide field of view volumetric image that is composed of volume segments and accompanied by a first comparative ECG display.

FIG. 6 illustrates an ultrasound display in accordance with the principles of the present invention in which the wide field of view volume 70 is composed of four volume segments 80, 82, 84, and 86. The volume segments were acquired during four cardiac cycles, the ECG waveforms 92, 94, 96, 98 of which are shown in a comparable display 90. By "comparable" it is meant that significant disparities between the waveforms are readily observable. In this embodiment the waveforms 92, 94, 96, 98 are comparable by reason of their alignment one above the other. It is seen that in this embodiment the ECG waveforms 92, 94, 96, 98 are substantially identical. This uniform appearance of the waveforms gives assurance to the user that all of the segments are substantially in phase and contain no significant artifacts due to an arrhythmic heartbeat. The user is thus given the confidence that the volume 70 is diagnostic.

When the volume 70 is played in real time the volume rendered images are stored in Cineloop memory. To show the heart or other anatomy in consecutive phases of the heart cycle, these stored images are generally played in a repeating loop, which is usually a single heart cycle in length. The loop may be played in real time, in slow motion, or in stop action. In this example a single heart cycle is shown repeatedly as the loop replays. To the right of the ECG display 90 is a vertical line which moves through the ECG waveforms as the loop plays, indicating the instantaneous phase of the heart being shown at that moment. This vertical line is known as a frame position indicator. The frame position indicator thus repeatedly moves through the waveforms and if the playing of the loop is stopped the frame position indicator stops to indicate the phase of the heart then frozen on the display. On either side of the frame position indicator is a triangular carat called an edit marker. The left (start) edit marker can be moved to the left to indicate the desired starting point of the loop in the heart cycle and the right (stop) edit marker can be moved to the right of the edit start marker to select a desired ending point for the loop. With these markers a loop can be defined for replay which is a subset of the full loop of image frames.

Figure 8:
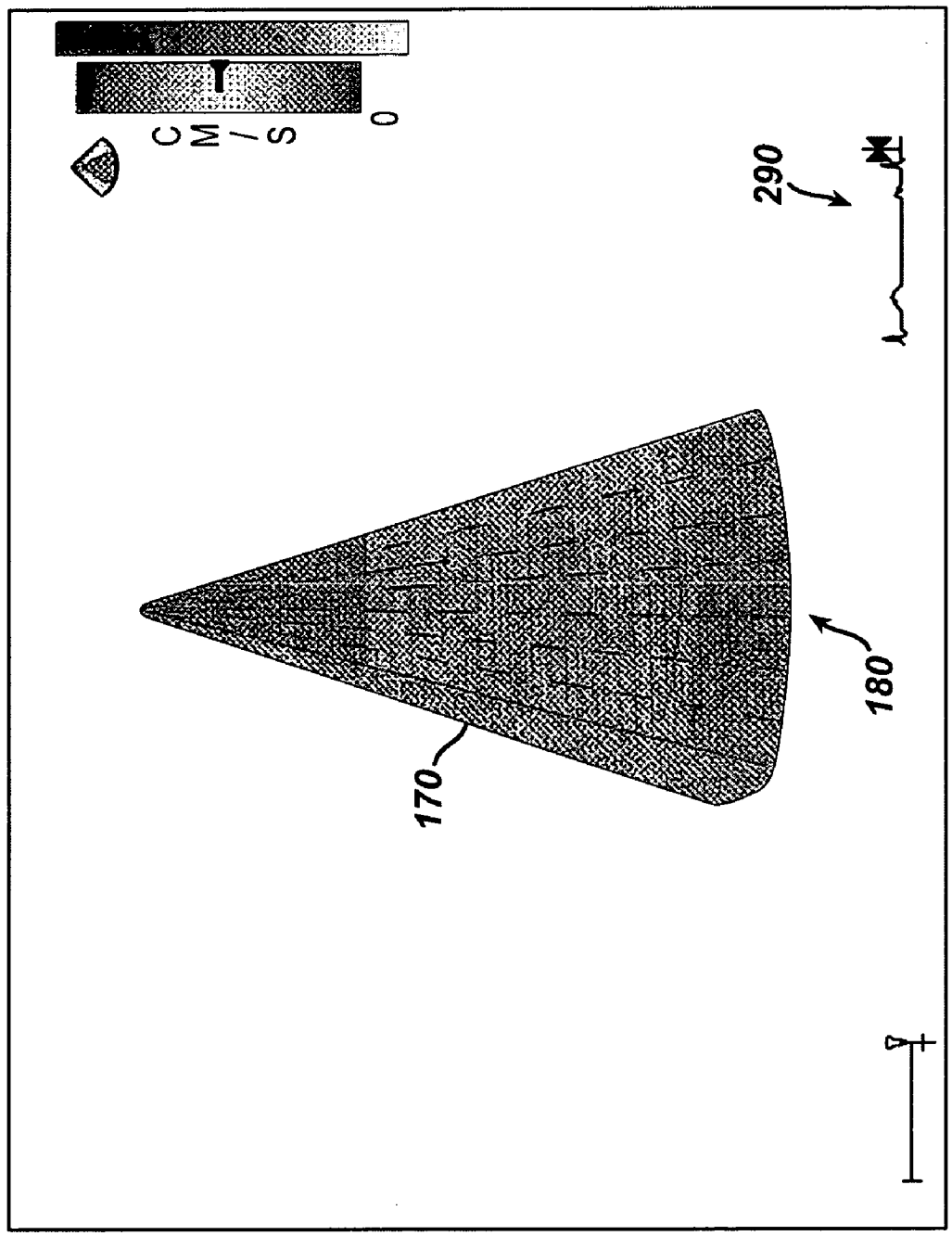
FIG. 8 shows a third embodiment of an ultrasound display of a wide field of view volumetric image that is composed of volume segments and accompanied by a second comparative ECG display.
Figure 9:
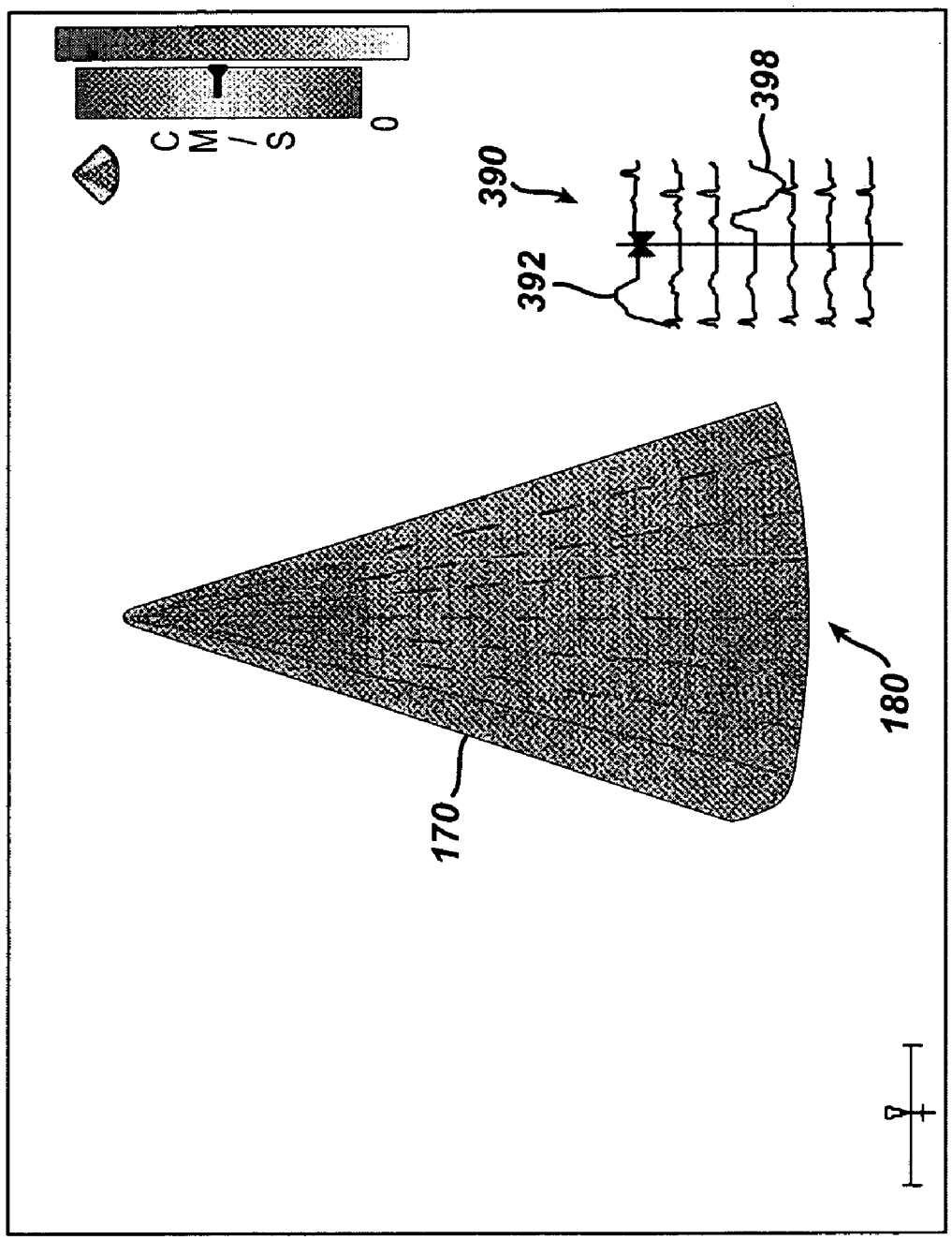
FIG. 9 shows a first example of an ultrasound display of a wide field of view volumetric image and an ECG display during an arrhythmic condition.
Figure 10:
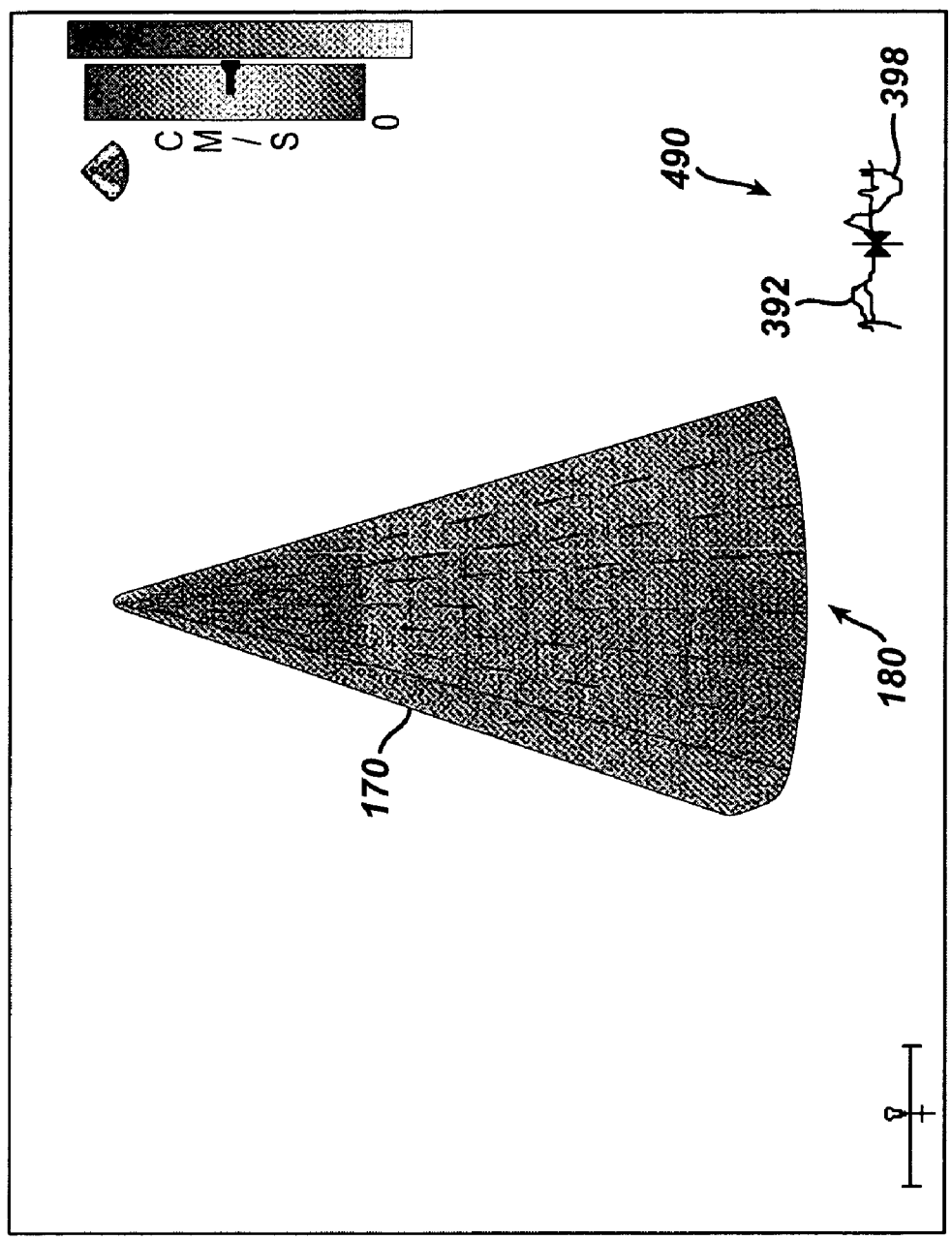
FIG. 10 shows a second example of an ultrasound display of a wide field of view volumetric image and an ECG display during an arrhythmic condition.

FIG. 7 illustrates another display of the present invention which shows a wide field of view volume 170 composed of seven volume segments 180. The ECG waveforms of the heart cycles during which these volume segments were acquired are shown in the comparable display 190. In this embodiment the waveforms of the display 190 are visually distinctive, either by different shading or coloring. The volume segments can be correspondingly marked with the demarcating shades or coloring if desired. While the display 190 readily shows any significant disparity in the waveforms due to their vertical alignment, the distinctive appearances of the waveforms can also be used in the comparable display 290 of FIG. 8. In this embodiment differently colored or shaded waveforms are displayed aligned in time (horizontally, generally by alignment of the R-wave peaks or alignment to the time of start of volume segment acquisition) and also on top of each other (vertically aligned). In this example, since the ECG waveforms 190 are generally uniform, the horizontal and vertical alignment 290 appears substantially as one ECG waveform, showing that the ECG waveforms are all substantially identical and that there are no heartbeat irregularity artifacts in the wide field of view image 170.

However, an arrhythmic heartbeat could result in irregular ECG waveforms such as waveforms 392 and 398 of the comparable display 390. When the seven waveforms of the display 390 are shown in an overlapping display 490 like that of FIG. 8, the differently colored or shaded irregular waveforms 392 and 398 readily stand out. The user is thus alerted by the comparable displays 390 or 490 that the wide field of view image 170 probably contains arrhythmic heartbeat artifacts, with the colors or shades of the comparable displays 390,490 indicating exactly which volume segments are likely to be affected.

Once an irregular ECG waveform and suspect volume segment have been identified, the user can ignore the wide field of view-image and acquire another one which hopefully will not be so contaminated. Another possibility is to reacquire the affected segment or segments and replace the contaminated segments with good ones. This necessitates that there be no significant motion in the interim and that the probe is held stationary throughout the initial acquisition interval and during the reacquisition interval. Yet a further possibility is to analyze the ECG waveforms automatically and automatically reacquire any volume segment that is suspect. In the embodiment of FIG. 1 this may be done by sampling each ECG waveform and applying the sampled waveforms to the signal processor 28. The signal processor aligns and compares the waveforms by correlation or other comparing process to see whether they are identical within a defined range or limit of deviation from an average or from each other. When a waveform is acquired which exceeds the desired range or limit of deviation, a signal is sent back to the system controller 32 over line 50, informing the controller of the volume segment which needs to be reacquired. The system controller then controls the ultrasound system to reacquire the indicated volume segment and replace the suspect volume segment in the image data buffer 38 with the data set of the reacquired volume segment. Thus, volume segments affected by heartbeat irregularity are identified and replaced rapidly, on the fly, without the need for user intervention.

It will be appreciated that the volume segments can be highlighted or colored to correspond to their respective ECG waveforms as desired. For example, when the user points to one of the ECG waveforms on the display screen, the corresponding volume segment of the three-dimensional image 70 can be automatically highlighted or colored to indicate the volume segment corresponding to the ECG waveform. The volume segments can be outlined in color or otherwise distinctively marked to visually correspond to a particular ECG waveform, for instance.

What is claimed is:

1. A method for medical ultrasound imaging, comprising:
   acquiring ultrasound image data representative of three-dimensional volume segments of an image volume in synchronism with cardiac cycles of a subject, each of the volume segments containing image data distributed in three dimensions which is acquired during a cardiac cycle of the subject;
   acquiring ECG waveforms of the cardiac cycles during which the volume segments are acquired;
   combining the image data representative of the volume segments to provide image data representative of a three-dimensional ultrasound image of the image volume; and
   displaying the ECG waveforms in a comparative display in which the uniformity of the waveforms is illustrated in association with the volume segments to which each of the ECG waveforms corresponds.

2. The method of claim 1, further comprising displaying the three-dimensional ultrasound image of the image volume concurrently with the comparative display of ECG waveforms.

3. The method of claim 1, wherein displaying the ECG waveforms in a comparative display comprises displaying the ECG waveforms in separate lines in which the waveforms are vertically aligned by their R-waves.

4. The method of claim 3, wherein displaying the ECG waveforms in a comparative display further comprises displaying the ECG waveforms in different visually distinctive ways.

5. The method of claim 4, wherein displaying the ECG waveforms in different visually distinctive ways comprises displaying the ECG waveforms in different shadings.

6. The method of claim 4, wherein displaying the ECG waveforms in different visually distinctive ways comprises displaying the ECG waveforms in different colors.

7. The method of claim 1, wherein displaying the ECG waveforms in a comparative display comprises displaying the ECG waveforms in overlapping alignment.

8. The method of claim 1, wherein displaying the ECG waveforms in a comparative display further comprises displaying the ECG waveforms in different colors.

9. A method for medical ultrasound imaging, comprising:
acquiring ultrasound image data representative of three-dimensional volume segments of an image volume in synchronism with cardiac cycles of a subject, each of the volume segments containing image data distributed in three dimensions which is acquired during a cardiac cycle of the subject;
acquiring ECG waveforms of the cardiac cycles during which the volume segments are acquired;
comparing the ECG waveforms;
reacquiring the ultrasound image data of a volume segment having an ECG waveform which is dissimilar from the ECGwavefom,s of other volume segments;
combining the image data representative of the volume segments to provide image data representative of a three-dimensional ultrasound image of the image volume; and
displaying a three-dimensional ultrasound image of the image volume.

10. A medical diagnostic ultrasound imaging system comprising:
a transducer comprising an array of transducer elements;
a transmitter for transmitting ultrasound energy with said transducer into volume segments of an image volume of interest in a subject as a plurality of transmit beams;
a receiver for receiving ultrasound echoes with said transducer from the image volume in response to the ultrasound energy and for generating received signals representative of the received ultrasound echoes;
a receive beamformer for processing said received signals to form at least one receive beam for each of the transmit beams and to generate image data representative of the ultrasound echoes in the receive beam;
an image memory which stores the image data of a plurality of volume segments;
an ECG device coupled to the subject for generating an ECG signal representative of the cardiac cycle during reception of echoes from a volume segment; and
a display for displaying an image volume and the ECG signals of the volume segments of the image volume in a comparative display in which each volume segment is associated with the ECG signal of the cardiac cycle occurring during the reception of echoes from that volume segment.

11. The medical diagnostic ultrasound imaging system of claim 10, wherein the display further comprises a display of the ECG signals of the volume segments which are in vertical alignment.

12. The medical diagnostic ultrasound imaging system of claim 11, wherein the display further comprises a display of the ECG signals of the volume segments in different colors.

13. The medical diagnostic ultrasound imaging system of claim 11, wherein the display further comprises a display of the ECG signals of the volume segments which are vertically aligned by their R-waves.

14. The medical diagnostic ultrasound imaging system of claim 10, wherein the display further comprises a display of the ECG signals of the volume segments in different colors.

15. The medical diagnostic ultrasound imaging system of claim 10, wherein the display further comprises a display of the ECG signals of the volume segments in overlapping alignment.

16. The medical diagnostic ultrasound imaging system of claim 15, wherein the display further comprises a display of the ECG signals of the volume segments in different colors.

* * * * *